United States Patent
Saito et al.

(10) Patent No.: US 9,211,241 B2
(45) Date of Patent: Dec. 15, 2015

(54) ORAL COMPOSITION

(71) Applicant: Kao Corporation, Chuo-ku, Tokyo (JP)

(72) Inventors: Takuya Saito, Ichikawa (JP); Yoshitaka Yano, Suginami-ku (JP); Mika Nagayama, Koto-ku (JP); Misato Honda, Kamagaya (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 14/400,644

(22) PCT Filed: Jun. 7, 2013

(86) PCT No.: PCT/JP2013/065786
§ 371 (c)(1),
(2) Date: Nov. 12, 2014

(87) PCT Pub. No.: WO2013/183748
PCT Pub. Date: Dec. 12, 2013

(65) Prior Publication Data
US 2015/0098911 A1    Apr. 9, 2015

(30) Foreign Application Priority Data

Jun. 8, 2012 (JP) ................................. 2012-131288
Jun. 8, 2012 (JP) ................................. 2012-131306
Dec. 5, 2012 (JP) ................................. 2012-266282

(51) Int. Cl.
| | | |
|---|---|---|
| *A61K 8/24* | (2006.01) |
| *A61K 8/60* | (2006.01) |
| *A61K 8/44* | (2006.01) |
| *A61K 8/34* | (2006.01) |
| *A61K 8/46* | (2006.01) |
| *A61Q 11/00* | (2006.01) |
| *A61K 8/37* | (2006.01) |
| *A61K 8/55* | (2006.01) |

(52) U.S. Cl.
CPC ... *A61K 8/24* (2013.01); *A61K 8/34* (2013.01); *A61K 8/345* (2013.01); *A61K 8/37* (2013.01); *A61K 8/44* (2013.01); *A61K 8/46* (2013.01); *A61K 8/463* (2013.01); *A61K 8/55* (2013.01); *A61K 8/60* (2013.01); *A61Q 11/00* (2013.01)

(58) Field of Classification Search
USPC .................................. 424/54, 49; 514/259.31
IPC .......................................................... A61K 8/49
See application file for complete search history.

(56) References Cited

U.S. PATENT DOCUMENTS

| 4,865,839 A | 9/1989 | Saso |
| 5,017,364 A | 5/1991 | Mitsutake et al. |
| 5,900,230 A * | 5/1999 | Cutler ............................ 424/49 |

FOREIGN PATENT DOCUMENTS

| JP | 54-117039 A | 9/1979 |
| JP | 63-060917 A | 3/1988 |
| JP | 02-256608 A | 10/1990 |
| JP | 3-200714 A | 9/1991 |
| JP | 09-012438 A | 1/1997 |
| JP | 10-017444 A | 1/1998 |
| JP | 11-021219 A | 1/1999 |
| JP | 2005-029506 A | 2/2005 |
| JP | 2007-161657 A | 6/2007 |
| JP | 2008-143824 A | 6/2008 |
| JP | 2010-143843 A | 7/2010 |

OTHER PUBLICATIONS

International Search Report (ISR) for PCT/JP2013/065786; I.A. fd: Jun. 7, 2013, mailed Sep. 10, 2013, the Japanese Patent Office, Tokyo, Japan.
International Preliminary Report on Patentability (IPRP) including the Written Opinion of the International Searching Authority (PCT Rule 44bis) for PCT/JP2013/065786; I.A. fd: Jun. 7, 2013, issued Dec. 9, 2014, by the International Bureau of WIPO, Geneva, Switzerland.

\* cited by examiner

*Primary Examiner* — Walter Webb
(74) *Attorney, Agent, or Firm* — Sterne, Kessler, Goldstein & Fox P.L.L.C.

(57) ABSTRACT

Provided is an oral composition that can sufficiently remove protein staining present on a tooth surface, can effectively prevent adhesion of protein staining on a tooth surface and can provide a good actual feeling of the cleaning effect in the oral cavity. The oral composition comprises the following components (A) and (B): (A) an N-acylamino acid or a salt thereof in an amount of 0.005 mass % or more and 0.3 mass % or less; and (B) pyrophosphoric acid or a salt thereof in an amount of 0.005 mass % or more and 0.5 mass % or less, in which a mass ratio ((B)/(A)) of the component (B) to the component (A) is 0.05 or more and 40 or less and a total content of the component (A) and the component (B) is 0.01 mass % or more and 0.6 mass % or less.

25 Claims, 2 Drawing Sheets

ORAL COMPOSITION

FIELD OF THE INVENTION

The present invention relates to an oral composition.

BACKGROUND OF THE INVENTION

Heretofore, various surfactants have been used as a foaming agent to enhance dispersibility of components blended and to improve a feeling upon use and a cleansing effect in an oral composition. For example, Patent Document 1 discloses a dentifrice composition in which an N-long-chain acyl glutamate is blended as the surfactant. In an oral composition described in Patent Document 2, there is made an attempt to further provide an effect of inhibiting the formation of stain by blending an amino acid-based surfactant. Further, an acylamino acid salt that is known as an amino acid-based surfactant having less skin and mucosal irritation may provide bitterness. Therefore, for example, Patent Document 3 discloses an oral composition that maintains good taste by blending an acylamino acid salt in as small an amount as 0.5 mass % or less and has a foaming ability enhanced by using a glucose fatty acid ester in addition to the acylamino acid salt.

On the other hand, it is known that blending of a pyrophosphate or the like can prevent the adhesion of dirt to a tooth surface. For example, Patent Document 4 discloses an oral composition including an alkyl sulfate, 1 wt % or more of a water-soluble polyphosphate such as a pyrophosphate and an orthophosphate. The document describes that the composition can enhance a chemical cleaning effect against dirt such as stain, plaque or tobacco tar on a tooth surface. Further, Patent Document 5 discloses a dentifrice composition in which an anionic surfactant, 0.3 to 1.5 mass % of a water-soluble pyrophosphate and specific hydroxypropyl cellulose are blended to exhibit an excellent tooth dirt-removing effect.

CITATION LIST

Patent Document

[Patent Document 1] JP-A-2-256608
[Patent Document 2] JP-A-10-17444
[Patent Document 3] JP-A-3-200714
[Patent Document 4] JP-A-9-12438
[Patent Document 5] JP-A-2007-161657

SUMMARY OF THE INVENTION

The various dirt such as stain, plaque and tobacco tar adhering to a tooth surface is made by forming a layer including bacterial coaggregation or another inorganic dirt on protein staining formed on the tooth surface. Therefore, the protein staining that is present between the tooth surface and the dirt such as stain or plaque is effectively removed, resulting in that the dirt such as stain or plaque can be removed completely to enhance a cleansing effect. Further, an effect of suppressing the formation of plaque can be highly expected by preventing the adhesion of protein staining to the tooth surface. Further, although details of a process of dental calculus formation are not completely clarified, it is considered that the dental calculus is formed by a calcification phenomenon of plaque, which is caused by the adhesion of calcium and phosphorus supplied from saliva or effusion to bacteria that form the plaque present on a tooth surface or an organic substrate such as adhesive dextran and the crystallization of the thus-adhered complex. The inorganic component is a hydroxyapatite-like calcific substance.

Therefore, the effect of suppressing the formation of plaque can be highly expected if it is possible to prevent the adhesion of protein staining to the tooth surface and to suppress the transition of a calcium phosphate component deposited in plaque to hydroxyapatite crystals and the growth of the crystals. Further, tooth decay can be effectively prevented if it is possible to impart acid resistance capable of effectively suppressing the elution of calcium ions from a tooth surface.

In general, a tooth cleaning effect of an oral composition is examined in many cases on whether a user himself or herself can actually feel smoothness when touching the tooth surface with his or her tongue or the like except that the effect is judged by a specialist such as a doctor or a dental hygienist. Therefore, an oral composition capable of providing the cleaning effect that can be easily and actually felt by a user is preferred. Further, it is desired that use of the oral composition can enhance resistance to tooth decay and can provide good taste.

However, as mentioned in Patent Documents 1 to 3, even when amino acid-based surfactants are used, it is impossible to provide an ability to remove protein staining on teeth. Further, depending on a component used in combination and the amount of the component blended, it may be difficult to provide good taste. Further, as mentioned in Patent Documents 4 and 5, even when a polyphosphate such as a pyrophosphate is blended, a user may not actually feel a sufficient cleaning effect because both of the effect of removing protein staining and the effect of preventing the adhesion of protein staining are not sufficiently achieved, and the feeling of teeth after cleansing of the oral cavity may be deteriorated as the amount of the polyphosphate blended is increased. Further, in all the documents as described above, no study has been made on enhancement of acid resistance and imparting of good low-temperature stability.

Therefore, the present invention relates to an oral composition that can sufficiently remove protein staining present on a tooth surface, can effectively prevent the adhesion of protein staining on a tooth surface and can satisfactorily provide realization of a cleaning effect of the oral composition, and further has excellent acid resistance or good low-temperature stability and can enhance taste and a feeling upon use.

Therefore, the inventors of the present invention made various studies and found that when an oral composition comprises specific amounts of an N-acylamino acid or a salt thereof and pyrophosphoric acid or a salt thereof at a specific ratio in a specific total amount, such an oral composition could be obtained that enhanced effect of removing protein staining and effect of preventing the adhesion of protein staining and was able to provide an actual feeling of good cleaning effect in the oral cavity, and further had excellent acid resistance or good low-temperature stability.

Further, the inventors found that the oral composition of the present invention was expected to provide a more excellent effect of suppressing the formation of plaque because the composition was able to suppress transition of a calcium phosphate component deposited in plaque to hydroxyapatite crystals and growth of the crystals.

Further, the inventors found that the oral composition of the present invention had excellent acid resistance, and hence the composition was able to effectively suppress the elution of calcium ions from a tooth surface, was able to maintain good stability under a low-temperature environment and was able to suppress an expression of unpleasant taste such as bitterness or salty taste to provide good taste.

That is, the present invention relates to an oral composition, comprising the following components (A) and (B):

(A) an N-acylamino acid or a salt thereof in an amount of 0.005 mass % or more and 0.3 mass % or less; and (B) pyrophosphoric acid or a salt thereof in an amount of 0.005 mass % or more and 0.5 mass % or less, in which a mass ratio ((B)/(A)) of the component (B) to the component (A) is 0.05 or more and 40 or less and a total content of the component (A) and the component (B) is 0.01 mass % or more and 0.6 mass % or less.

The oral composition of the present invention has excellent effect of removing protein staining on a tooth surface and effect of suppressing the adhesion of protein staining to a tooth surface, can provide an actual feeling of slippery and smooth tooth surface after use of the oral composition, can be sufficiently expected to provide an effect of suppressing the formation of plaque and can realize an increased cleaning effect, and further has excellent acid resistance or good low-temperature stability and has good taste.

DETAILED DESCRIPTION OF THE INVENTION

Figure 1:
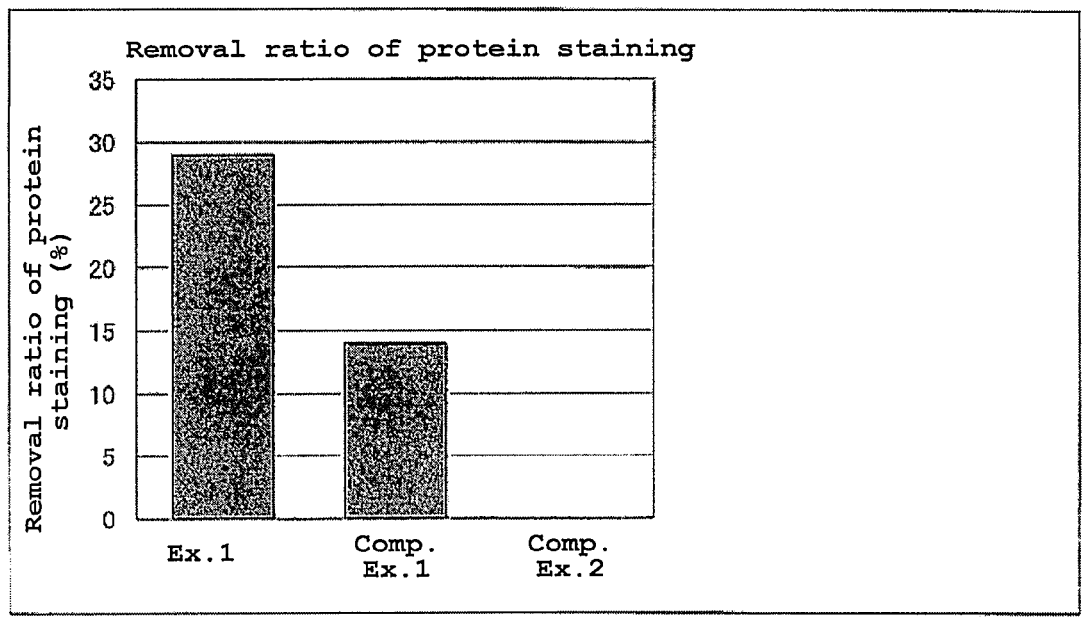
FIG. 1 is a graph showing results of evaluation of an effect of removing protein staining. The vertical axis represents a removal ratio (%) of protein staining.

Hereinafter, the present invention is described in detail.

An oral composition of the present invention comprises an N-acylamino acid or a salt thereof (A) in an amount of 0.005 mass % or more and 0.3 mass % or less. When the composition comprises the component (A) in a specific amount, the component (A) can effectively remove protein staining and can effectively suppress the adhesion of protein staining together with a specific amount of pyrophosphoric acid or a salt thereof (B) to be described below. Further, in the oral cavity after use of the oral composition of the present invention, the composition can enhance a slippery feeling without causing a coarse feeling of having something caught, which can be achieved in a condition of a smooth tooth surface with no dirt adhering thereto, and can sufficiently realize a so-called increased cleaning effect. Further, the composition can suppress the expression of bitterness specific to the component (A), and hence can achieve a good balance between excellent cleansing performance and good taste. In this description, the smooth feeling without causing a coarse feeling of having something caught refers to a smooth feeling of a tooth surface where the tongue can be moved almost without feeling any friction when the tongue touches the tooth surface.

The acyl group in the N-acylamino acid is derived from a saturated or unsaturated and linear or branched fatty acid or a mixed fatty acid thereof, preferably a linear fatty acid or a mixed fatty acid of linear fatty acids, and is preferably an acyl group having 6 to 22 carbon atoms, more preferably an acyl group having 10 to 20 carbon atoms, more preferably an acyl group having 10 to 18 carbon atoms, even more preferably an acyl group having 12 to 18 carbon atoms, from the viewpoint of providing both of the excellent effect of removing protein staining and the excellent effect of suppressing the adhesion of protein staining, the viewpoint of realizing an excellent cleaning effect and the viewpoint of providing excellent acid resistance and good low-temperature stability. The acyl group is preferably one kind or two or more kinds selected from a capryloyl group, a lauroyl group, a myristoyl group, a palmitoyl group, a stearoyl group and a cocoyl group, more preferably one kind or two or more kinds selected from a lauroyl group, a myristoyl group and a cocoyl group, even more preferably one or more kinds selected from a lauroyl group and a myristoyl group, from the viewpoints of foaming and ease in handling of the oral composition.

The amino acid moiety in the N-acylamino acid is preferably one kind or two or more kinds selected from glutamic acid, aspartic acid, glycine, alanine, threonine, methylalanine, sarcosine, lysine and arginine. The amino acid moiety in the N-acylamino acid is preferably an acidic amino acid, more preferably one or more kinds selected from glutamic acid and aspartic acid, even more preferably glutamic acid, from the viewpoint of improving the effect of removing protein staining and the effect of preventing the adhesion of dirt together with the component (B) and the viewpoint of providing excellent acid resistance and good low-temperature stability. Further, the amino acid moiety may be a D-isomer, an L-isomer or a mixture of the D-isomer and the L-isomer, preferably an L-isomer.

The N-acylamino acid or the salt thereof (A) is preferably one or more kinds selected from N-lauroyl glutamic acid, N-myristoyl glutamic acid, N-cocoyl glutamic acid, N-lauroyl aspartic acid and salts thereof, more preferably one or more kinds selected from N-lauroyl glutamic acid, N-myristoyl glutamic acid, N-cocoyl glutamic acid and salts thereof, even more preferably one or more kinds selected from N-lauroyl glutamic acid, N-myristoyl glutamic acid and salts thereof, from the viewpoints of providing an effect of removing protein staining, an effect of suppressing the adhesion of protein staining, excellent acid resistance and good low-temperature stability.

Examples of the salt of the N-acylamino acid salt include: alkali metal salts of sodium, potassium and the like; alkaline earth metal salts of calcium, magnesium and the like; other inorganic salts of aluminum, zinc and the like; an ammonium salt; organic amine salts of monoethanolamine, diethanolamine, triethanolamine and the like; and basic amino acid salts of arginine, lysine, histidine, ornithine and the like. One kind of those may be used singly, or two or more kinds thereof may be used in combination. Of those, the salt of the N-acylamino acid salt is preferably an alkali metal salt, more preferably a sodium salt, from the viewpoints of flavor and easy availability.

The content of the N-acylamino acid or the salt thereof (A) in the oral composition of the present invention is 0.005 mass % or more, preferably 0.007 mass % or more, more preferably 0.01 mass % or more, from the viewpoint of drastically enhancing the effect of removing protein staining and the effect of suppressing the adhesion of protein staining together with pyrophosphoric acid or a salt thereof used as the component (B) described below, the viewpoint of realizing a cleaning effect, the viewpoint of taste and the viewpoints of providing excellent acid resistance and good low-temperature stability. The content of the N-acylamino acid or the salt thereof (A) in the oral composition of the present invention is 0.3 mass % or less, preferably 0.2 mass % or less, more preferably 0.1 mass % or less, from the viewpoints of improving the effect of removing protein staining and the effect of suppressing the adhesion of protein staining together with the component (B) described below, suppressing bitterness and harshness, and realizing a cleaning effect. Further, the content of the N-acylamino acid or the salt thereof (A) in the oral composition of the present invention is from 0.005 to 0.3 mass %, preferably from 0.007 to 0.2 mass %, more preferably from 0.01 to 0.1 mass %.

The oral composition of the present invention comprises a pyrophosphoric acid or the salt thereof (B) in an amount of 0.005 mass % or more and 0.5 mass % or less. When the composition comprises the component (B) in a specific amount, the component (B) can drastically enhance the effect of removing protein staining and the effect of suppressing the adhesion of protein staining together with the component (A), can sufficiently realize an increased cleaning effect in the oral cavity after use of the composition and can provide excellent acid resistance and good low-temperature stability. The salt of the pyrophosphoric acid salt is preferably a sodium salt or a potassium salt from the viewpoint of solubility in water, and one kind of the pyrophosphoric acid or the salt thereof (B) may be used singly, or two or more kinds thereof may be used in combination. Of those, the pyrophosphoric acid or the salt thereof (B) is preferably sodium pyrophosphate from the viewpoint of the effect of removing protein staining and the effect of suppressing the adhesion of protein staining and the viewpoint of providing excellent acid resistance and good low-temperature stability.

The content of the pyrophosphoric acid or the salt thereof (B) in the oral composition of the present invention is 0.005 mass % or more, preferably 0.007 mass % or more, more preferably 0.01 mass % or more, from the viewpoint of synergistically enhancing the effect of removing protein staining and the effect of suppressing the adhesion of protein staining together with the component (A), the viewpoint of realizing a cleaning effect and the viewpoint of providing excellent acid resistance and good low-temperature stability. The content of the pyrophosphoric acid or the salt thereof (B) in the oral composition of the present invention is 0.5 mass % or less, preferably 0.4 mass % or less, more preferably 0.15 mass % or less, from the viewpoints of suppressing a coarse feeling, suppressing to poorly realize a cleaning effect and preventing deterioration of flavor. Further, the content of the pyrophosphoric acid or the salt thereof (B) in the oral composition of the present invention is from 0.005 to 0.5 mass %, preferably from 0.007 to 0.5 mass %, more preferably from 0.01 to 0.5 mass %, more preferably from 0.01 to 0.4 mass %, even more preferably 0.01 to 0.15 mass %.

The total of the content of the N-acylamino acid or the salt thereof (A) and the content of the pyrophosphoric acid or the salt thereof (B) is 0.01 mass % or more, preferably 0.02 mass % or more, from the viewpoint of realizing a cleaning effect while synergistically enhancing the effect of removing protein staining and the effect of suppressing the adhesion of protein staining, and the viewpoint of providing excellent acid resistance and good low-temperature stability. Further, the total content of the component (A) and the component (B) is 0.6 mass % or less, preferably 0.45 mass % or less, more preferably 0.3 mass % or less, even more preferably 0.2 mass % or less, from the viewpoint of enhancing the effect of removing protein staining of teeth and the effect of suppressing the adhesion of protein staining to teeth, the viewpoint of realizing a cleaning effect and the viewpoint of taste. Further, the total content of the component (A) and the component (B) is from 0.01 to 0.6 mass %, preferably from 0.01 to 0.45 mass %, more preferably from 0.02 to 0.45 mass %, more preferably from 0.02 to 0.3 mass %, even more preferably from 0.02 to 0.2 mass %.

The mass ratio ((B)/(A)) of the pyrophosphoric acid or the salt thereof (B) to the N-acylamino acid or the salt thereof (A) is 0.05 or more, preferably 0.1 or more, and is 40 or less, preferably 15 or less, more preferably 12 or less, from the viewpoint of synergistically enhancing the effect of removing protein staining and the effect of suppressing the adhesion of protein staining while maintaining good flavor, the viewpoint of realizing a cleaning effect and the viewpoint of providing excellent acid resistance and good low-temperature stability. Further, the mass ratio ((B)/(A)) is from 0.05 to 40, preferably from 0.1 to 40, more preferably from 0.1 to 15, even more preferably from 0.1 to 12.

The oral composition of the present invention preferably further includes an alkyl sulfate (C) in an amount of 0.5 mass % or more and 2 mass % or less, from the viewpoint of ensuring a good feeling upon use while suppressing reduction in foaming by the component (A) and the viewpoint of achieving a good balance between the effect of suppressing the adhesion of protein staining and the effect of removing protein staining, and in the case where the oral composition of the present invention is a dentifrice composition as described below. Specifically, the alkyl sulfate is, for example, one or more kinds selected from sodium lauryl sulfate, sodium myristyl sulfate, sodium palmityl sulfate, sodium stearyl sulfate, sodium octyl sulfate and sodium capryl sulfate. Of those, the alkyl sulfate (C) is preferably sodium lauryl sulfate from the viewpoint of providing the effect of removing protein staining while ensuring the effect of suppressing the adhesion of protein staining.

The content of the alkyl sulfate (C) in the oral composition of the present invention is preferably 0.5 mass % or more, more preferably 0.8 mass % or more, even more preferably 1 mass % or more, and is preferably 2 mass % or less, more preferably 1.7 mass % or less, even more preferably 1.5 mass % or less, from the viewpoint of ensuring good foaming, the effect of suppressing the adhesion of protein staining and a good feeling upon use. Further, the content of the alkyl sulfate (C) in the oral composition of the present invention is preferably from 0.5 to 2 mass %, more preferably from 0.8 to 1.7 mass %, even more preferably from 1 to 1.5 mass %.

The mass ratio ((C)/(A)) of the alkyl sulfate (C) to the N-acylamino acid or the salt thereof (A) is preferably 5 or more, more preferably 10 or more, and is preferably 200 or less, more preferably 150 or less, from the viewpoint of sufficiently achieving the effect of suppressing the adhesion of protein staining while maintaining good foaming. Further, the mass ratio ((C)/(A)) is preferably from 5 to 200, more preferably from 10 to 150.

The oral composition of the present invention preferably further includes a sugar alcohol (D) that is dissolved in an aqueous solution at 20° C. in an amount of from 5 to 40 g with respect to 100 g of the aqueous solution, from the viewpoints of enhancing a refreshing effect and realizing an enhanced cleaning effect and the viewpoint of ameliorating bitterness specific to the component (A), harshness and the like. Note that the aqueous solution refers to an aqueous solution obtained by dissolving the sugar alcohol (D) in water. As such sugar alcohol (D), one or more kinds selected from erythritol, mannitol, α-D-glucopyranosyl-1,6-sorbitol, α-D-glucopyranosyl-1,6-mannitol and reduced palatinose, which is a mixture of α-D-glucopyranosyl-1,6-sorbitol and α-D-glucopyranosyl-1,6-mannitol, are preferred from the viewpoints of a refreshing feeling and good flavor in the oral cavity; erythritol or reduced palatinose is more preferred from the viewpoints of appropriate solubility and taste and erythritol is even more preferred from the viewpoint of a good refreshing feeling.

The content of the component (D) in the oral composition of the present invention is preferably 20 mass % or more, more preferably 25 mass % or more, even more preferably 30 mass % or more, and is preferably 60 mass % or less, more preferably 55 mass % or less, even more preferably 50 mass % or less, from the viewpoint of providing a clear and refreshing effect and the viewpoint of sustaining good taste. Further, the content of the component (D) in the oral composition of the present invention is preferably from 20 to 60 mass %, more preferably from 25 to 55 mass %, even more preferably from 30 to 50 mass %.

The oral composition of the present invention preferably further includes another sugar alcohol other than the component (D), that is dissolved in an aqueous solution at 20° C. in an amount of more than 40 g with respect to 100 g of the aqueous solution, from the viewpoints of taste and a feeling upon use. The sugar alcohol other than the component (D) is preferably selected from sorbitol and xylitol, and is preferably sorbitol capable of acting as a wetting agent. The content of the sugar alcohol other than the component (D) in the oral composition of the present invention is preferably 10 mass % or more, more preferably 15 mass % or more, and is preferably 30 mass % or less, from the viewpoint of a feeling upon use. Note that, when the oral composition of the present invention is a liquid oral composition, the content of the sugar alcohol other than the component (D) in the oral composition of the present invention is preferably 10 mass % or less, more preferably 8 mass % or less, and is preferably 1 mass % or more, more preferably 2 mass % or more, from the viewpoints of taste and a feeling upon use and the viewpoint of preventing deposition on an opening of a container or the like.

The form of the oral composition of the present invention is not particularly limited as long as the composition can be applied in the mouth, and the composition may be used as a dentifrice composition such as a toothpaste or tooth powder, or as a liquid oral composition such as a mouthwash or a liquid dentifrice. Of those, the oral composition of the present invention is preferably a liquid oral composition selected from a mouthwash and a liquid dentifrice, from the viewpoints of good effect of removing protein staining and effect of suppressing the adhesion of protein staining and the viewpoint of realizing an increased cleaning effect, and is preferably a toothpaste from the viewpoint of enhancing the effect of removing protein staining and the effect of suppressing the adhesion of protein staining in combination with physical cleansing using a toothbrush.

The oral composition of the present invention includes water in addition to the components described above. This can appropriately spread the component (A) and the component (B) in the oral cavity while dissolving or dispersing the components to effectively achieve the effect of removing protein staining and the effect of suppressing the adhesion of protein staining.

For example, when the oral composition of the present invention is a dentifrice composition, the content of the water in 100 mass % of the dentifrice composition of the present invention is preferably 10 mass % or more, more preferably 12 mass % or more, and is preferably 60 mass % or less, more preferably 50 mass % or less. Further, when the oral composition of the present invention is a dentifrice composition, the content of the water in 100 mass % of the dentifrice composition of the present invention is preferably from 10 to 60 mass %, more preferably from 12 to 50 mass %.

For example, when the oral composition of the present invention is a liquid oral composition, the content of the water in 100 mass % of the liquid oral composition of the present invention is preferably 50 mass % or more, more preferably 70 mass % or more, even more preferably 80 mass % or more. The content of the water in 100 mass % of the liquid oral composition of the present invention is the rest of other components and is preferably 99.99 mass % or less, more preferably 99.98 mass % or less, even more preferably less than 99.98 mass %. Further, when the oral composition of the present invention is a liquid oral composition and further includes a non-ionic surfactant (F), the content of the water in 100 mass % of the liquid oral composition of the present invention is preferably 50 mass % or more, more preferably 70 mass % or more, more preferably 80 mass % or more, even more preferably 86 mass % or more, and is preferably 99 mass % or less, more preferably 95 mass % or less, even more preferably less than 92 mass %. Further, when the oral composition of the present invention is a liquid oral composition, the content of the water in 100 mass % of the liquid oral composition of the present invention is preferably from 50 to 99.99 mass %, more preferably from 70 to 99.98 mass %, more preferably from 80 to 90 mass %, more preferably from 86 to 95 mass %, even more preferably from 86 to 92 mass %.

When the oral composition of the present invention is a dentifrice composition, its water content can be calculated on the basis of the content of water blended and the water content in the components blended, and can also be measured with, for example, a Karl Fischer moisture titrator. For example, a trace moisture titrator (Hiranuma Sangyo Co., Ltd.) can be used as the Karl Fischer moisture titrator. 5 g of the dentifrice composition is suspended in 25 g of anhydrous methanol, yielding a suspension and the water content of the dentifrice composition can be measured with 0.02 g of the suspension by using the titrator.

When the oral composition of the present invention is a dentifrice composition, the composition preferably further includes a binder (E). As the binder (E), there may be used one or more kinds selected from the group consisting of, for example, sodium alginate, sodium carboxymethyl cellulose, carrageenan, xanthan gum, sodium polyacrylate, hydroxyethyl cellulose, hydroxypropyl cellulose, pectin, gum tragacanth, gum arabic, guar gum, gum karaya, locust bean gum, gellan gum, tamarind gum, *psyllium* seed gum, polyvinyl alcohol, sodium chondroitin sulfate and a methoxyethylene-maleic anhydride copolymer. Of those, the binder (E) is preferably one or more kinds selected from sodium carboxymethyl cellulose having a degree of etherification of from 0.7 to 2.0, carrageenan and xanthan gum, more preferably two or more kinds selected from the foregoing.

The content of the binder (E) in the oral composition for oral cavity of the present invention is preferably 0.3 mass % or more, more preferably 0.4 mass % or more, and is preferably 2 mass % or less, more preferably 1.5 mass % or less. Further, the content of the binder (E) in the oral composition of the present invention is preferably from 0.3 to 2 mass %, more preferably from 0.4 to 1.5 mass %. Note that, when the oral composition of the present invention is a dentifrice composition, the composition preferably includes thickening silica (having an oil absorption of from 200 to 400 mL/100 g measured by a method in accordance with JIS K5101-13-2) in an amount of 1 mass % or more and 12 mass % or less together with the binder (E).

When the oral composition of the present invention is a dentifrice composition, the composition may further include an abrasive as long as the effects of the present invention are not impaired. Examples of the abrasive include calcium phosphate, calcium hydrogen phosphate, calcium carbonate, aluminum hydroxide, aluminum silicate, zirconium silicate, abrasive silica (having an oil absorption of from 50 to 150 mL/100 g measured by a method in accordance with JIS K5101-13-2) and the like. An abrasive having a radioactive dentin abrasion value (RDA value, which is a value obtained by measurement in accordance with ISO11609, Test method for abrasive property, Attachment A) of from 20 to 250 is generally used as the abrasive. The oral composition of the present invention realizes an excellent cleaning effect in addition to provision of high effect of removing protein staining and effect of suppressing the adhesion of protein staining. Therefore, even when the content of the abrasive is reduced, an excellent effect can be achieved. The content of the abrasive in the oral composition of the present invention is preferably 1 mass % or more, and is preferably 20 mass % or less, more preferably 10 mass % or less.

The oral composition of the present invention preferably further includes a non-ionic surfactant (F). When the composition includes the component (F), it is possible to enhance acid resistance to effectively suppress the elution of calcium ions from a tooth surface and to impart good low-temperature stability. Further, it is possible to effectively suppress the adhesion of a calcium phosphate component deposited in plaque to hydroxyapatite. Examples of the component (F) include a polyglycerin fatty acid ester, a sucrose fatty acid ester, and polyoxyethylene hydrogenated castor oil having the average addition molar number of less than 60, preferably the average addition molar number of 40 or less. One kind of those may be used singly, or two or more kinds thereof may be used in combination. Of those, one or more kinds selected from a polyglycerin fatty acid ester and a sucrose fatty acid ester are preferred from the viewpoints of effectively enhancing acid resistance and suppressing the adhesion of calcium phosphate and the viewpoint of effectively imparting low-temperature stability.

The polyglycerin fatty acid ester used as the component (F) is derived from preferably a fatty acid having 12 to 20 carbon atoms, more preferably a fatty acid having 12 to 18 carbon atoms. Further, the polyglycerin fatty acid ester used as the component (F) has the average glycerin condensation degree of preferably from 2 to 20, more preferably from 5 to 12.

The sucrose fatty acid ester used as the component (F) is derived from preferably a fatty acid having 6 to 20 carbon atoms, more preferably a fatty acid having 10 to 18 carbon atoms, even more preferably a fatty acid having 12 to 14 carbon atoms.

The content of the component (F) in the oral composition of the present invention is preferably 0.01 mass % or more, more preferably 0.05 mass % or more, more preferably 0.1 mass % or more, even more preferably 0.15 mass % or more, from the viewpoints of enhancing acid resistance and suppressing the adhesion of calcium phosphate and the viewpoint of imparting low-temperature stability. The content of the component (F) in the oral composition of the present invention is preferably 2 mass % or less, more preferably 1 mass % or less, even more preferably 0.8 mass % or less, from the viewpoints of taste and a feeling upon use. Further, the content of the component (F) in the oral composition of the present invention is preferably from 0.01 to 2 mass %, more preferably from 0.05 to 1 mass %, more preferably from 0.1 to 0.8 mass %, even more preferably from 0.15 to 0.8 mass %.

The oral composition of the present invention preferably includes sucralose (G) from the viewpoints of further improving bitterness specific to the component (A), salty taste specific to the component (B), and, for example, strong bitterness and harshness caused by coexistence of the components (A) to (C). The content of the component (G) in the oral composition of the present invention is preferably 0.001 mass % or more, more preferably 0.005 mass % or more, even more preferably 0.008 mass % or more. The content of the sucralose (G) in the oral composition of the present invention is preferably 0.1 mass % or less, more preferably 0.03 mass % or less, even more preferably 0.02 mass % or less, from the viewpoint of preventing deterioration of a refreshing feeling of the oral composition. Note that the sucralose is otherwise known as 4,1',6'-trichlorogalactosucrose, has a structure obtained by substituting three of hydroxyl groups of sucrose selectively by chlorine atoms, and is available from San-Ei Gen F.F.I., Inc. or the like.

The mass ratio ((A)+(B))/(G) of the N-acylamino acid or the salt thereof (A) and the pyrophosphoric acid or the salt thereof (B) to the sucralose (G) is preferably 0.5 or more, more preferably 1 or more, even more preferably 1.5 or more, from the viewpoint of more ensuring a good balance between excellent cleansing performance and realization of good taste. The mass ratio ((A)+(B))/(G) is preferably 30 or less, more preferably 25 or less, even more preferably 12 or less, from the viewpoint of more ensuring a good balance between realization of a cleaning effect and actualization of good taste. Further, the mass ratio ((A)+(B))/(G) is preferably from 0.5 to 30, more preferably from 1 to 25, even more preferably from 1.5 to 12.

The oral composition of the present invention preferably further includes glycerin (H) from the viewpoint of ensuring good taste. The content of the component (H) in the oral composition of the present invention is preferably 1 mass % or more, more preferably 2 mass % or more, and is preferably 10 mass % or less, more preferably 8 mass % or less.

The oral composition of the present invention preferably includes a flavor composition from the viewpoint of improving taste together with the component (G). An example of the flavor composition is a flavor composition containing: a sesquiterpene-based hydrocarbon such as pinene, myrcene, limonene, terpinene or cymene; a sesquiterpene-based aldehyde such as citral, citronellal or perillaldehyde; citrus-based oil such as orange, lemon or lime oil; a phenyl ether such as anethole; an aromatic alcohol such as thymol or eugenol; or a natural essential oil of bergamot or the like. One kind of those may be used singly, or two or more kinds thereof may be used in combination. Of those, the flavor composition is preferably a flavor composition containing a flavor selected from anethole, thymol and eugenol, from the viewpoints of providing good sweetness and alleviating the expression of bitterness, more preferably a flavor composition containing at least anethole. The anethole is contained in the flavor composition preferably in an amount of 0.3 mass % or more and 20 mass % or less.

The oral composition of the present invention may further include, for example: fluoride ion supplying compounds such as tin fluoride, sodium fluoride and ammonium fluoride and a fluoride such as sodium monofluorophosphate; and, in addition, ingredients for hypersensitive dentin such as aluminum lactate, calcium phosphate, hydroxyapatite and arginine-calcium carbonate, wetting agents other than sorbitol and glycerin such as polyethylene glycol and propylene glycol; a sweetener other than sucralose; a flavor; a pH adjuster; a bactericide such as a cationic bactericide; an antiinflammatory agent; an antiseptic; a plant extract; and other active ingredients as long as the effects of the present invention are not impaired.

With regard to the embodiments described above, the present invention further discloses the following oral composition:

[1] An oral composition, comprising the following components (A) and (B):

(A) an N-acylamino acid or a salt thereof in an amount of 0.005 mass % or more and 0.3 mass % or less; and (B) pyrophosphoric acid or a salt thereof in an amount of 0.005 mass % or more and 0.5 mass % or less, in which a mass ratio ((B)/(A)) of the component (B) to the component (A) is 0.05 or more and 40 or less, and a total content of the component (A) and the component (B) is 0.01 mass % or more and 0.6 mass % or less.

[2] The oral composition according to the above-mentioned item [1], in which the mass ratio ((B)/(A)) of the component (B) to the component (A) is 0.05 or more, preferably 0.1 or more, and is 40 or less, preferably 15 or less, more preferably 12 or less.

[3] The oral composition according to the above-mentioned item [1] or [2], in which the total content of the component (A) and the component (B) is 0.01 mass % or more, preferably 0.02 mass % or more, and is 0.6 mass % or less, preferably 0.45 mass % or less, more preferably 0.3 mass % or less.

[4] The oral composition according to any one of the above-mentioned items [1] to [3], in which the content of the component (A) is 0.005 mass % or more, preferably 0.007 mass % or more, more preferably 0.01 mass % or more, and is 0.3 mass % or less, preferably 0.2 mass % or less, more preferably 0.1 mass % or less.

[5] The oral composition according to any one of the above-mentioned items [1] to [4], in which the component (A) has preferably an acyl group having 6 to 22 carbon atoms, more preferably an acyl group having 10 to 20 carbon atoms, more preferably an acyl group having 10 to 18 carbon atoms, even more preferably an acyl group having 12 to 18 carbon atoms.

[6] The oral composition according to any one of the above-mentioned items [1] to [5], in which the component (A) is preferably an N-acyl acidic amino acid or a salt thereof.

[7] The oral composition according to any one of the above-mentioned items [1] to [6], in which the component (A) is preferably one or more kinds selected from N-lauroyl glutamic acid, N-myristoyl glutamic acid, N-cocoyl glutamic acid, N-lauroyl aspartic acid and salts thereof, more preferably one or more kinds selected from N-lauroyl glutamic acid, N-myristoyl glutamic acid, N-cocoyl glutamic acid and salts thereof, even more preferably one or more kinds selected from N-lauroyl glutamic acid, N-myristoyl glutamic acid and salts thereof.

[8] The oral composition according to any one of the above-mentioned items [1] to [7], in which the content of the component (B) is 0.005 mass % or more, preferably 0.007 mass % or more, more preferably 0.01 mass % or more, and is 0.5 mass % or less, preferably 0.4 mass % or less, more preferably 0.15 mass % or less.

[9] The oral composition according to any one of the above-mentioned items [1] to [8], in which the component (B) is preferably pyrophosphoric acid or an alkali metal salt thereof, more preferably sodium pyrophosphate.

[10] The oral composition according to any one of the above-mentioned items [1] to [9], further comprising (C) an alkyl sulfate.

[11] The oral composition according to the above-mentioned item [10], in which the component (C) is preferably one or more kinds selected from sodium lauryl sulfate, sodium myristyl sulfate, sodium palmityl sulfate, sodium stearyl sulfate, sodium octyl sulfate and sodium capryl sulfate, more preferably sodium lauryl sulfate.

[12] The oral composition according to the above-mentioned item [10] or [11], in which the content of the component (C) is preferably 0.5 mass % or more, more preferably 0.8 mass % or more, even preferably 1 mass % or more, and is preferably 2 mass % or less, more preferably 1.7 mass % or less, even more preferably 1.5 mass % or less.

[13] The oral composition according to any one of the above-mentioned items [10] to [12], in which the mass ratio ((C)/(A)) of the component (C) to the component (A) is preferably 5 or more, more preferably 10 or more, and is preferably 200 or less, more preferably 150 or less.

[14] The oral composition according to any one of the above-mentioned items [1] to [13], further comprising (D) a sugar alcohol that is dissolved in an aqueous solution at 20° C. in an amount of from 5 to 40 g with respect to 100 g of the aqueous solution.

[15] The oral composition according to the above-mentioned item [14], in which the component (D) is preferably one or more kinds selected from erythritol, mannitol, α-D-glucopyranosyl-1,6-sorbitol, α-D-glucopyranosyl-1,6-mannitol and reduced palatinose, which is a mixture of α-D-glucopyranosyl-1,6-sorbitol and α-D-glucopyranosyl-1,6-mannitol, more preferably erythritol.

[16] The oral composition according to the above-mentioned item [14] or [15], in which the content of the component (D) is preferably 20 mass % or more, more preferably 25 mass % or more, even more preferably 30 mass % or more, and is preferably 60 mass % or less, more preferably 55 mass % or less, even more preferably 50 mass % or less.

[17] The oral composition according to any one of the above-mentioned items [1] to [16], further comprising another sugar alcohol other than the component (D).

[18] The oral composition according to any one of the above-mentioned items [1] to [17], in which, when the oral composition is a dentifrice composition, the content of water is preferably 10 mass % or more, more preferably 12 mass % or more, and is preferably 60 mass % or less, more preferably 50 mass % or less, and when the oral composition is a liquid oral composition, the content of water is preferably 50 mass % or more, more preferably 70 mass % or more, even more preferably 80 mass % or more, and is preferably 99.99 mass % or less, more preferably 99.98 mass % or less, even more preferably less than 99.98 mass %.

[19] The oral composition according to any one of the above-mentioned items [1] to [18], further including an abrasive at 1 mass % or more and 20 mass % or less, more preferably 1 mass % or more and 10 mass % or less.

[20] The oral composition according to any one of the above-mentioned items [1] to [19], further comprising (E) a binder.

[21] The oral composition according to the above-mentioned item [20], in which the content of the component (E) is preferably 0.3 mass % or more, more preferably 0.4 mass % or more, and is preferably 2 mass % or less, more preferably 1.5 mass % or less.

[22] The oral composition according to any one of the above-mentioned items [1] to [21], further comprising (F) a non-ionic surfactant.

[23] The oral composition according to the above-mentioned item [22], in which the component (F) comprises preferably one or more kinds selected from a polyglycerin fatty acid ester and a sucrose fatty acid ester.

[24] The oral composition according to the above-mentioned item [22] or [23], in which the polyglycerin fatty acid ester used as the component (F) is derived from preferably a fatty acid having 12 to 20 carbon atoms, more preferably a fatty acid having 12 to 18 carbon atoms.

[25] The oral composition according to any one of the above-mentioned items [22] to [24], in which the polyglycerin fatty acid ester used as the component (F) has an average glycerin condensation degree of preferably from 2 to 20, more preferably from 5 to 12.

[26] The oral composition according to the above-mentioned item [22], in which the sucrose fatty acid ester used as the component (F) is derived from preferably a fatty acid having 6 to 20 carbon atoms, more preferably a fatty acid having 10 to 18 carbon atoms, even more preferably a fatty acid having 12 to 14 carbon atoms.

[27] The oral composition according to any one of the above-mentioned items [22] to [26], in which the content of the component (F) is preferably 0.01 mass % or more, more preferably 0.05 mass % or more, more preferably 0.1 mass % or more, even more preferably 0.15 mass % or more, and is preferably 2 mass % or less, more preferably 1 mass % or less, even more preferably 0.8 mass % or less.

[28] The oral composition according to any one of the above-mentioned items [1] to [27], further comprising (G) sucralose.

[29] The oral composition according to the above-mentioned item [28], in which the content of the component (G) is preferably 0.001 mass % or more, more preferably 0.005 mass % or more, even more preferably 0.008 mass % or more, and is preferably 0.1 mass % or less, more preferably 0.03 mass % or less, even more preferably 0.02 mass % or less.

[30] The oral composition according to the above-mentioned item [28] or [29], in which the mass ratio ((A)+(B))/(G) of the component (A) and the component (B) to the component (G) is preferably 0.5 or more, more preferably 1 or more, even more preferably 1.5 or more, and is preferably 30 or less, more preferably 25 or less, even more preferably 12 or less.

[31] The oral composition according to the above-mentioned items [1] to [30], further comprising (H) glycerin.

[32] The oral composition according to the above-mentioned item [31], in which the content of the component (H) is preferably 1 mass % or more, more preferably 2 mass % or more, and is preferably 10 mass % or less, more preferably 8 mass % or less.

[33] The oral composition according to the above-mentioned items [1] to [32], in which the oral composition is a dentifrice composition.

[34] The oral composition according to the above-mentioned items [1] to [32], in which the oral composition is a liquid oral composition.

[35] The oral composition according to the above-mentioned items [1] to [34], in which the oral composition is for application in an oral cavity.

[36] Use of the oral composition according to the above-mentioned items [1] to [34], for cleansing teeth.

[37] Use of the oral composition according to the above-mentioned items [1] to [34], for removing protein staining on a tooth surface or for suppressing the adhesion of protein staining to a tooth surface.

[38] Use of the oral composition according to the above-mentioned items [1] to [34], for improving acid resistance of teeth.

[39] The oral composition according to the above-mentioned items [1] to [34], in which the oral composition is for use in removing protein staining on a tooth surface or for suppressing the adhesion of protein staining to a tooth surface.

[40] The oral composition according to the above-mentioned items [1] to [34], in which the oral composition is for use in improving acid resistance of teeth.

[41] Use of the oral composition according to the above-mentioned items [1] to [34], for producing a cleansing agent for teeth.

[42] Use of the oral composition according to the above-mentioned items [1] to [34], for producing an agent for removing protein staining on a tooth surface or for producing an agent for suppressing the adhesion of protein staining to a tooth surface.

[43] Use of the oral composition according to the above-mentioned items [1] to [34], for producing an agent for improving acid resistance of teeth.

[44] A method of cleansing teeth, comprising applying the oral composition according to the above-mentioned items [1] to [34] to teeth.

[45] A method of removing protein staining on a tooth surface or a method of suppressing the adhesion of protein staining to a tooth surface, comprising applying the oral composition according to the above-mentioned items [1] to [34] to teeth.

[46] A method of improving acid resistance of teeth, comprising applying the oral composition according to the above-mentioned items [1] to [34] to teeth.

EXAMPLES

Hereinafter, the present invention is specifically described by way of Examples. Note that the content of each component is represented in a mass % unit unless otherwise specifically stated in tables.

Examples 1 to 9 and Comparative Examples 1 to 4

Liquid oral compositions adjusted to pH 7 were prepared according to the compositions shown in Tables 1 and 2, and were used to perform the evaluation of effect of removing protein staining, effect of suppressing the adhesion of protein staining and cleansing performance in accordance with the following methods.

Note that the liquid oral compositions shown in Tables 1 and 2 were prepared so that the total amount was 100 mass %.

<<Test for Evaluation of Effect of Removing Protein Staining>>

50 mg of hydroxyapatite (HAp) powder (HAP-200, Taihei Chemical Industrial Co., Ltd.) was mixed with 5 ml of purified water to produce a suspension. Subsequently, 15 mg of albumin (derived from bovine serum, Wako Pure Chemical Industries, Ltd., pH 5.2) was added to the suspension, and the mixture was left with shaking for 90 minutes. Note that the shaking was carried out using a shaking machine (CUTE MIXER CM-1000 (EYERA Tokyo Rikakikai Co., LTD.)).

After that, the HAp in the suspension was centrifuged (3,000 rmp, 5 minutes), and the supernatant was removed by suction, followed by repeating washing (5 mL of purified water were added, the mixture was centrifuged again, and the supernatant was removed by suction) twice. The HAp after washing and 5 mL of purified water were mixed to produce a suspension, and a 75-µL aliquot was taken out from the suspension and centrifuged again. Then, the supernatant was removed by suction to prepare HAp for evaluation of the liquid oral compositions. 1 mL of each liquid oral composition was added to the HAp after washing, and the mixture was stirred for 2 minutes. Subsequently, the mixture was centrifuged, and the supernatant was removed by suction, followed by washing with 300 mL of purified water in the same manner as above. 100 µL of 1 N hydrochloric acid and 1 mL of phosphate buffer (0.1 mol, pH 8.4) were added to the HAp after washing, and the mixture was stirred to prepare a solution. A 400-µL aliquot was taken out from the solution, and 150 µL of a fluorochrome solution (a solution of 0.3 mg/mL fluorescamine in acetone) were added, followed by mixing. Further, a 200-µL aliquot was taken out from the mixed solution obtained by mixing the fluorochrome solution and left to stand still in the dark for 30 minutes. Note that all procedures in the test including still standing were carried out at room temperature (20° C.).

Next, the amount of proteins remaining in the HAp (amount of residual proteins) was determined by measuring fluorescence. The fluorescence was measured using a microplate fluorophotometer Gemini EM (Molecular Devices Corporation) at an excitation light wavelength of 360 nm and a fluorescence wavelength of 480 nm. A calibration curve was created based on the results of fluorescence measurement of phosphate buffer solutions containing various concentrations of albumin (0.1 mol phosphate buffer, pH 8.4), and the results of fluorescence measurement were converted into amounts of residual proteins.

The amount of residual proteins was determined in the same manner as in the evaluation test described above except that purified water was used instead of the liquid oral composition. The resultant value was defined as 100, and the removal ratio of proteins (%) was calculated based on the amount of residual proteins, which was determined for each liquid oral composition. Tables 1 and 2 show the results, and FIG. 1 shows the results of Example 1 and Comparative Examples 1 and 2.

<<Test for Evaluation of Effect of Suppressing Adhesion of Protein Staining>>

50 mg of hydroxyapatite (HAp) powder (HAP-200, Taihei Chemical Industrial Co., Ltd.) was mixed with 5 ml of purified water to produce a suspension. Next, a 75-μL aliquot of the HAp suspension was taken out and centrifuged (3,000 rpm, 5 minutes), and the supernatant was removed by suction to prepare HAp for evaluation of the liquid oral compositions. 1 mL of each liquid oral composition was added to the HAp after washing, and the mixture was stirred for 2 minutes, followed by washing with 300 mL of purified water twice in the same manner as above. Subsequently, 75 μL of an aqueous albumin solution (derived from bovine serum, Wako Pure Chemical Industries, Ltd., pH 5.2, 3 mg/mL) was added thereto, and the mixture was left with shaking for 90 minutes in the same manner as above. Next, the mixture was centrifuged (3,000 rmp, 5 minutes), and the supernatant was removed by suction, followed by washing with 300 mL of purified water twice in the same manner as above. 100 μL of 1 N hydrochloric acid and 1 mL of phosphate buffer (0.1 mol, pH 8.4) were added to the HAp after washing, and the mixture was stirred. Then, a 400-μL aliquot was taken out, and 150 μL of a fluorochrome solution (a solution of 0.3 mg/mL fluorescamine in acetone) were mixed therein. Further, a 200-μL aliquot of the solution obtained by mixing the fluorochrome solution was taken out and left to stand still in the dark for 30 minutes. After still standing, the amount of proteins adhered to the HAp (amount of proteins adhered) was determined by fluorescence measurement in the same manner as above.

Figure 2:
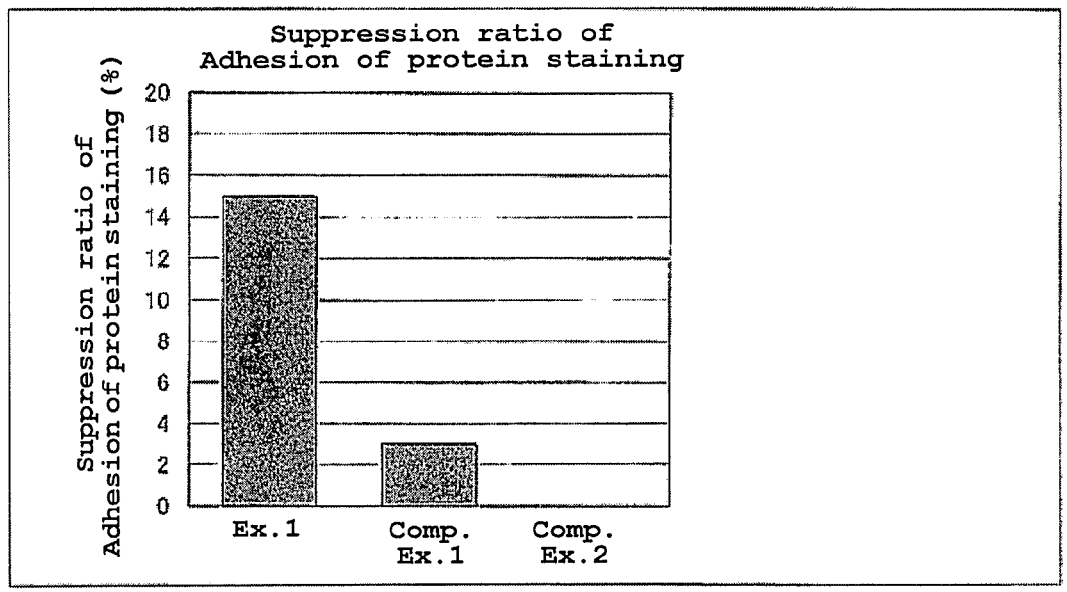
FIG. 2 is a graph showing results of evaluation of a suppression ratio of adhesion of protein staining. The vertical axis represents a suppression ratio (%) of adhesion of protein staining.

The amount of proteins adhered was determined in the same manner as above except that purified water was used instead of the liquid oral composition in the test for evaluation of the effect of suppressing the adhesion of protein staining. The resulting value was defined as 100, and the suppression ratio of protein staining (%) was calculated based on the amount of residual proteins, which was determined for each liquid oral composition. Tables 1 and 2 show the results, and FIG. 2 shows the results of Example 1 and Comparative Examples 1 and 2.

TABLE 1

| Composition (mass %) | Example 1 | Example 2 | Example 3 | Example 4 | Example 5 | Example 6 | Example 7 | Example 8 | Comparative Example 1 | Comparative Example 2 |
|---|---|---|---|---|---|---|---|---|---|---|
| (A) Sodium N-myristoyl-L-glutamate | 0.01 | — | 0.01 | 0.01 | 0.01 | 0.01 | 0.1 | 0.2 | — | 0.01 |
| Sodium N-lauroyl-L-glutamate | — | 0.01 | — | — | — | — | — | — | — | — |
| (B) Sodium pyrophosphate | 0.01 | 0.02 | 0.02 | 0.1 | 0.2 | 0.4 | 0.01 | 0.02 | 0.01 | — |
| pH adjuster (adjusted to pH 7) | Small amount | Small amount | Small amount | Small amount | Small amount | Small amount | Small amount | Small amount | Small amount | Small amount |
| Purified water | Balance | Balance | Balance | Balance | Balance | Balance | Balance | Balance | Balance | Balance |
| Water content | 99.98 | 99.97 | 99.97 | 99.89 | 99.79 | 99.59 | 99.89 | 99.78 | 99.99 | 99.99 |
| (B)/(A) | 1 | 2 | 2 | 10 | 20 | 40 | 0.1 | 0.1 | — | 0 |
| (A) + (B) | 0.02 | 0.03 | 0.03 | 0.11 | 0.21 | 0.41 | 0.11 | 0.22 | 0.01 | 0.01 |
| Evaluation | | | | | | | | | | |
| Removal ratio of protein staining (%) | 29 | 26 | 42 | 69 | 82 | 99 | 33 | 34 | 14 | 0 |
| Suppression ratio of adhesion of protein staining (%) | 15 | 26 | 30 | 15 | 24 | 28 | 32 | 23 | 3 | —[*1] |

[*1] Not measurable because the component (A) adhering to HAp caused water repelling

TABLE 2

| | Composition (mass %) | Example 9 | Comparative Example 3 | Comparative Example 4 |
|---|---|---|---|---|
| (A) | Sodium N-myristoyl-L-glutamate | 0.01 | 0 | 0.01 |
| (B) | Sodium pyrophosphate | 0.02 | 0 | 0 |
| (C) | Sodium lauryl sulfate | 1 | 1 | 1 |
| | pH adjuster | Small amount | Small amount | Small amount |
| | Purified water | Balance | Balance | Balance |
| | Water content | 98.97 | 99 | 98.99 |
| (B)/(A) | | 2 | — | — |
| (A) + (B) | | 0.03 | 0 | 0.01 |
| (C)/(A) | | 100 | — | 100 |
| Evaluation | | | | |
| Removal ratio of protein staining (%) | | 18 | −10 | −50 |
| Suppression ratio of adhesion of protein staining (%) | | 14 | — | — |

The results shown in Table 1 and FIGS. 1 and 2 reveal that the composition of Example 1 containing both the component (B) in an amount of 0.01 mass % and the component (A) in an amount of 0.01 mass % exhibited a removal ratio of protein staining about twice as high as that of the composition of Comparative Example 1 containing the component (B) alone in an amount of 0.01 mass %, and had drastically improved suppression ratio of adhesion of protein staining, although the composition of Comparative Example 2 containing the component (A) alone in an amount of 0.01 mass % had no effect of removing protein staining.

Further, the results shown in Table 2 revealed that the composition of Example 9 had excellent effect of removing protein staining and effect of suppressing the adhesion of protein staining as compared to the composition of Comparative Examples 3 and 4.

The results clearly indicate that, when the oral composition of the present invention contains specific amounts of the component (A) and component (B) described above at a specific mass ratio in a specific total amount, the composition has excellent cleaning performance for exhibiting high effect of removing protein staining and effect of suppressing the adhesion of protein staining and can sufficiently exhibit the effect provided by combination use of the component (A) and the component (B), as compared to a composition in which the component (A) or the component (B) is used singly.

Examples 10 to 19 and Comparative Examples 5 to 8

Dentifrice compositions having the compositions shown in Tables 3 and 4 were prepared and were used for the evaluation of a feeling on the tooth surface after use and the evaluation of taste in accordance with the following methods.

Tables 3 and 4 show the results.

<<Feeling of Tooth Surface after Use>>

1 g of each dentifrice composition obtained was placed on a toothbrush, and teeth were brushed for 2 minutes therewith. After that, the oral cavity was rinsed with water several times, and then the feeling of the tooth surfaces when the teeth were touched with the tongue was evaluated according to the following criteria. Two expert panelists evaluated the composition, and Table 2 shows the results of the evaluation through discussion.

AA: The teeth have smooth surfaces, and the composition realizes an increased cleaning effect.

A: The teeth have slightly coarse surfaces, but the composition realizes an increased cleaning effect.

B: The teeth have non-smooth surfaces, and the composition poorly realizes a cleaning effect.

C: The teeth have coarse surfaces (feel strong friction on the tooth surfaces).

<<Taste>>

1 g of each dentifrice composition obtained was placed on a toothbrush, and teeth were brushed for 2 minutes therewith. After that, the oral cavity was rinsed with water several times. The taste during brushing and the taste after rinse with water several times were evaluated according to the following criteria. Two expert panelists evaluated the composition, and Table 2 shows the results of the evaluation through discussion.

AA: Feel no bitterness, harshness, and salty taste.

A: Feel very slight bitterness, harshness, or salty taste.

B: Feel slight bitterness, harshness, or salty taste.

C: Feel bitterness, salty taste, and harshness.

CC: Feel very strong bitterness and harshness.

TABLE 3

| Composition (mass %) | Example 10 | Example 11 | Example 12 | Example 13 | Example 14 | Example 15 | Example 16 | Example 17 | Example 18 | Example 19 |
|---|---|---|---|---|---|---|---|---|---|---|
| (A) Sodium N-myristoyl-L-glutamate | 0.01 | — | 0.01 | 0.1 | 0.1 | 0.2 | 0.01 | 0.01 | 0.01 | 0.01 |
| Sodium N-lauroyl-L-glutamate | — | 0.01 | — | — | — | — | — | — | — | — |
| (B) Sodium pyrophosphate | 0.01 | 0.02 | 0.02 | 0.02 | 0.01 | 0.1 | 0.1 | 0.2 | 0.4 | 0.1 |
| (C) Sodium lauryl sulfate | 1.5 | 1.4 | 1.4 | 1.4 | 1.3 | 1 | 1.3 | 1.3 | 1.3 | 0.8 |
| (D) Erythritol | 40 | 40 | 40 | 40 | 40 | 40 | 40 | 40 | 40 | 30 |
| (E) Carboxymethyl cellulose | 0.3 | 0.3 | 0.3 | 0.3 | 0.3 | 0.3 | 0.3 | 0.3 | 0.3 | 1 |
| Xanthan gum | 0.05 | 0.05 | 0.05 | 0.05 | 0.05 | 0.05 | 0.05 | 0.05 | 0.05 | 0.1 |
| Carrageenan | 0.15 | 0.15 | 0.15 | 0.15 | 0.15 | 0.15 | 0.15 | 0.15 | 0.15 | — |
| (G) Sucralose | 0.005 | 0.01 | 0.01 | 0.01 | 0.01 | 0.02 | 0.01 | 0.01 | 0.02 | 0.01 |
| (H) Concentrated glycerin | 4 | 4 | 4 | 4 | 4 | 4 | 4 | 4 | 4 | 4 |
| Sorbitol solution (70%) | 30 | 30 | 30 | 30 | 30 | 30 | 30 | 30 | 30 | 20 |
| Polyethylene glycol | 5 | 5 | 5 | 5 | 5 | 5 | 5 | 5 | 5 | 4 |
| Abrasive silica | 6 | 6 | 6 | 6 | 6 | 6 | 6 | 6 | 6 | 5 |
| Thickening silica | 4.5 | 4.5 | 4.5 | 4.5 | 4.5 | 4.5 | 4.5 | 4.5 | 4.5 | 4.5 |
| Saccharin sodium | 0.03 | 0.03 | 0.03 | 0.03 | 0.03 | 0.03 | 0.03 | 0.03 | 0.03 | 0.03 |
| Titanium oxide | 0.3 | 0.3 | 0.3 | 0.3 | 0.3 | 0.3 | 0.3 | 0.3 | 0.3 | 0.3 |
| Flavor | 1 | 1 | 1 | 1 | 1 | 1 | 1 | 1 | 1 | 1 |
| Purified water | 7.145 | 7.23 | 7.23 | 7.14 | 7.25 | 7.35 | 7.25 | 7.15 | 6.94 | 29.15 |
| Water content | 16.145 | 16.23 | 16.23 | 16.14 | 16.25 | 16.35 | 16.25 | 16.15 | 15.94 | 35.15 |
| (B)/(A) | 1 | 2 | 2 | 0.2 | 0.1 | 0.5 | 10 | 20 | 40 | 10 |
| (A) + (B) | 0.02 | 0.03 | 0.03 | 0.12 | 0.11 | 0.3 | 0.11 | 0.21 | 0.41 | 0.11 |
| (C)/(A) | 150 | 140 | 140 | 14 | 13 | 5 | 130 | 130 | 130 | 80 |
| Evaluation | | | | | | | | | | |
| Feeling of tooth surface after use | AA | AA | AA | AA | AA | AA | AA | A | A | AA |
| Taste | A | AA | AA | A | A | B | AA | A | A | AA |

TABLE 4

| Composition (mass %) | Comparative Example 5 | Comparative Example 6 | Comparative Example 7 | Comparative Example 8 |
|---|---|---|---|---|
| (A) Sodium N-myristoyl-L-glutamate | 0.01 | 0.5 | — | 0.01 |
| (B) Sodium pyrophosphate | 1 | 1 | 0.02 | — |
| (C) Sodium lauryl sulfate | 1.3 | 1 | 1.3 | 1.3 |
| (D) Erythritol | 40 | 40 | 40 | 40 |
| (E) Carboxymethyl cellulose | 0.3 | 0.3 | 0.3 | 0.3 |
| Xanthan gum | 0.05 | 0.05 | 0.05 | 0.05 |
| Carrageenan | 0.15 | 0.15 | 0.15 | 0.15 |
| (G) Sucralose | 0.01 | 0.01 | 0.01 | 0.01 |
| (H) Concentrated glycerin | 4 | 4 | 4 | 4 |
| Sorbitol solution (70%) | 30 | 30 | 30 | 30 |
| Polyethylene glycol | 5 | 5 | 5 | 5 |
| Abrasive silica | 6 | 6 | 6 | 6 |
| Thickening silica | 4.5 | 4.5 | 4.5 | 4.5 |
| Saccharin sodium | 0.03 | 0.03 | 0.03 | 0.03 |
| Titanium oxide | 0.3 | 0.3 | 0.3 | 0.3 |
| Flavor | 1 | 1 | 1 | 1 |
| Purified water | 6.35 | 6.16 | 7.34 | 6.66 |
| Water content | 15.35 | 15.16 | 16.34 | 15.66 |
| (B)/(A) | 100 | 2 | — | 0 |
| (A) + (B) | 1.01 | 1.5 | 0.02 | 0.01 |
| (C)/(A) | 130 | 2 | — | 130 |
| Evaluation | | | | |
| Feeling of tooth surface after use | C | C | B | B |
| Taste | C | CC | AA | AA |

The results of Tables 3 and 4 reveal that, when the contents of the component (A) and the component (B) of the present invention are achieved, a smooth feeling of tooth surfaces after brushing (after washing) are provided and an increased cleaning effect are realized. On the other hand, when the content of sodium pyrophosphate used as the component (B) is large as in Comparative Examples 5 and 6, a cleaning effect is insufficiently realized because the tooth surfaces after brushing are not smooth and have a frictional feeling when touched with the tongue. Further, the compositions of Comparative Examples 5 and 6 included both the component (B) at a high content and the component (A), and hence were found to have bitterness, harshness, and salty taste. In particular, those foreign tastes were very strong in Comparative Example 6.

Comparative Examples 9 and 10

Comparison to Example 12

Dentifrice compositions having the compositions shown in Table 5 were prepared and were used for the evaluation of the suppression ratio of adhesion of protein staining by three panelists according to the following method. Table 5 shows the results of the evaluation including Example 12.

<<Evaluation of Suppression Ratio of Adhesion of Protein Staining in Human>>

Figure 3:
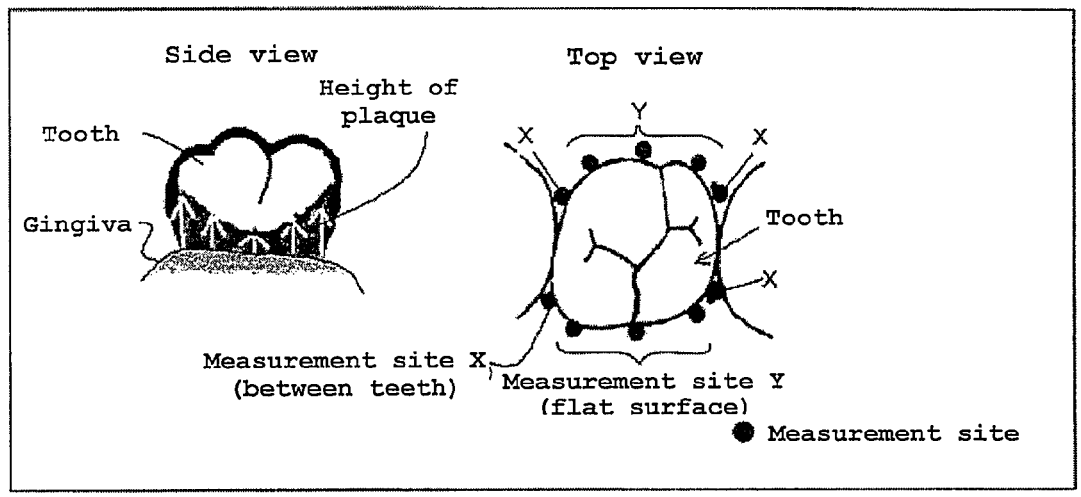
FIG. 3 is a schematic view illustrating sites where plaque amounts were measured.

1) A dental hygienist brushed teeth of a subject in advance until plaque disappeared.
2) 1 g of each dentifrice composition obtained was placed on a toothbrush, and the dental hygienist brushed the teeth for 2 minutes.
3) After that, the subject conducted a normal life for 24 hours without performing brushing of teeth, brushing or washing with a mouth rinse.
4) 24 hours later, the amount of plaque adhered to the teeth was measured. The amount of plaque was measured for 16 teeth including 4 teeth located at the top, bottom, left and right (teeth of Nos. 1, 4, 6, and 7) per subject. The measurement was carried out at a total of 10 sites including 4 sites located between teeth (measurement sites: X) and 6 sites located on flat surfaces (measurement sites: Y) as illustrated in FIG. 3. The amount of plaque was determined based on a height from the gingiva of a region of a tooth where plaque adhered for each measurement site as illustrated in FIG. 3. The amount of plaque for each dentifrice composition was defined as a total amount of the amounts determined by three panelists.

5) Note that the amount of plaque in the case where only teeth were brushed until the plaque disappeared without brushing with the dentifrice composition was defined as 100, and a difference from the amount of plaque determined for each dentifrice composition was determined as a decrease (amount of suppression of adhesion of protein staining) to calculate a suppression ratio of adhesion of protein staining (%).

TABLE 5

| Composition (mass %) | Example 12 | Comparative Example 9 | Comparative Example 10 |
|---|---|---|---|
| (A) Sodium N-myristoyl-L-glutamate | 0.01 | 0.15 | — |
| (B) Sodium pyrophosphate | 0.02 | — | — |
| (C) Sodium lauryl sulfate | 1.4 | 1.4 | 1.4 |
| (D) Erythritol | 40 | 40 | 40 |
| (E) Carboxymethyl cellulose | 0.3 | 0.3 | 0.3 |
| Xanthan gum | 0.05 | 0.05 | 0.05 |
| Carrageenan | 0.15 | 0.15 | 0.15 |
| (G) Sucralose | 0.01 | 0.01 | 0.01 |
| (H) Concentrated glycerin | 4 | 4 | 4 |
| Sorbitol solution (70%) | 30 | 30 | 30 |
| Polyethylene glycol | 5 | 5 | 5 |
| Abrasive silica | 6 | 6 | 6 |
| Thickening silica | 4.5 | 4.5 | 4.5 |
| Saccharin sodium | 0.03 | 0.03 | 0.03 |
| Titanium oxide | 0.3 | 0.3 | 0.3 |
| Flavor | 1 | 1 | 1 |
| Purified water | 7.23 | 7.11 | 7.26 |
| Water content | 16.23 | 16.11 | 16.26 |
| (B)/(A) | 2 | — | — |
| (A) + (B) | 0.03 | 0.15 | 0 |
| (C)/(A) | 140 | — | — |
| Suppression ratio of adhesion of protein staining (%) | 30 | 22 | 18 |

The results shown in Table 5 revealed that, when the oral composition of the present invention (dentifrice composition) including specific amounts of an N-acylamino acid or a salt thereof and pyrophosphoric acid or a salt thereof at a specific ratio in a specific total amount was applied to the oral cavity of a human, the composition provided good effect of suppressing the formation of plaque.

Examples 20 to 28 and Comparative Examples 11 to 14

Dentifrice compositions having the compositions shown in Table 6 were prepared and were used for the evaluation of a feeling of tooth surfaces after use and the evaluation of taste in the same manner as in Example 10 above. Note that the flavor used in Examples and Comparative Examples shown in Table 6 contained anethole in an amount of 5 mass % and contained limonene and pinene in a total amount of 10 mass % in 100 mass % of the flavor.

Table 6 shows the results.

TABLE 6

| | Composition (mass) | Example 20 | Example 21 | Example 22 | Example 23 | Example 24 | Example 25 | Example 26 | Example 27 | Example 28 | Comparative Example 11 | Comparative Example 12 | Comparative Example 13 | Comparative Example 14 |
|---|---|---|---|---|---|---|---|---|---|---|---|---|---|---|
| (A) | Sodium N-myristoyl-L-glutamate | 0.01 | — | 0.01 | 0.1 | 0.1 | 0.2 | 0.01 | 0.01 | 0.01 | 0.01 | 0.5 | — | 0.01 |
| | Sodium N-lauroyl-L-glutamate | — | 0.01 | — | — | — | — | — | — | — | — | — | — | — |
| (B) | Sodium pyrophosphate | 0.01 | 0.02 | 0.02 | 0.02 | 0.01 | 0.1 | 0.1 | 0.2 | 0.4 | 1 | 1 | 0.02 | — |
| (C) | Sodium lauryl sulfate | 1.5 | 1.4 | 1.4 | 1.4 | 1.3 | 1 | 1.3 | 1.3 | 1.3 | 1.3 | 1 | 1.3 | 1.3 |
| (D) | Erythritol | 40 | 40 | 40 | 40 | 40 | 40 | 40 | 40 | 40 | 40 | 40 | 40 | 40 |
| (E) | Carboxymethyl cellulose | 0.3 | 0.3 | 0.3 | 0.3 | 0.3 | 0.3 | 0.3 | 0.3 | 0.3 | 0.3 | 0.3 | 0.3 | 0.3 |
| | Xanthan gum | 0.05 | 0.05 | 0.05 | 0.05 | 0.05 | 0.05 | 0.05 | 0.05 | 0.05 | 0.05 | 0.05 | 0.05 | 0.05 |
| | Carrageenan | 0.15 | 0.15 | 0.15 | 0.15 | 0.15 | 0.15 | 0.15 | 0.15 | 0.15 | 0.15 | 0.15 | 0.15 | 0.15 |
| (G) | Sucralose | 0.005 | 0.01 | 0.01 | 0.01 | 0.01 | 0.02 | 0.01 | 0.01 | 0.02 | 0.01 | 0.01 | 0.01 | 0.01 |
| (H) | Concentrated glycerin | 4 | 4 | 4 | 4 | 4 | 4 | 4 | 4 | 4 | 4 | 4 | 4 | 4 |
| | Sorbitol solution (70%) | 28 | 28 | 28 | 28 | 28 | 28 | 28 | 28 | 28 | 28 | 28 | 28 | 28 |
| | Polyethylene glycol | 5 | 5 | 5 | 5 | 5 | 5 | 5 | 5 | 5 | 5 | 5 | 5 | 5 |
| | Abrasive silica | 6 | 6 | 6 | 6 | 6 | 6 | 6 | 6 | 6 | 6 | 6 | 6 | 6 |
| | Thickening silica | 4.5 | 4.5 | 4.5 | 4.5 | 4.5 | 4.5 | 4.5 | 4.5 | 4.5 | 4.5 | 4.5 | 4.5 | 4.5 |
| | Saccharin sodium | 0.03 | 0.03 | 0.03 | 0.03 | 0.03 | 0.03 | 0.03 | 0.03 | 0.03 | 0.03 | 0.03 | 0.03 | 0.03 |
| | Titanium oxide | 3 | 3 | 3 | 3 | 3 | 3 | 3 | 3 | 3 | 3 | 3 | 3 | 3 |
| | Flavor | 1 | 1 | 1 | 1 | 1 | 1 | 1 | 1 | 1 | 1 | 1 | 1 | 1 |
| | Purified water | 6.445 | 6.53 | 6.53 | 6.44 | 6.55 | 6.65 | 6.55 | 6.45 | 6.24 | 5.65 | 5.46 | 6.64 | 6.65 |
| | Water content | 14.845 | 14.93 | 14.93 | 14.84 | 14.95 | 15.05 | 14.95 | 14.85 | 14.64 | 14.05 | 13.86 | 15.04 | 15.05 |
| | (B)/(A) | 1 | 2 | 2 | 0.2 | 0.1 | 0.5 | 10 | 20 | 40 | 100 | 2 | — | 0 |
| | (A) + (B) | 0.02 | 0.03 | 0.03 | 0.12 | 0.11 | 0.3 | 0.11 | 0.21 | 0.41 | 1.01 | 1.5 | 0.02 | 0.01 |
| | (C)/(A) | 150 | 140 | 140 | 14 | 13 | 5 | 130 | 130 | 130 | 130 | 2 | — | 130 |
| | ((A) + (B))/(G) | 4 | 3 | 3 | 12 | 11 | 15 | 11 | 21 | 21 | 101 | 150 | — | — |
| | Evaluation | | | | | | | | | | | | | |
| | Feeling of tooth surface after use | AA | AA | AA | AA | AA | AA | AA | A | A | C | C | B | B |
| | Taste | A | AA | AA | A | A | B | AA | A | A | C | CC | AA | AA |

As shown in Table 6, the oral compositions of the present invention (dentifrice compositions) were found to provide smooth tooth surfaces after use, to realize an excellent cleaning effect, to suppress a foreign taste such as bitterness, harshness, or salty taste caused by a combination use of the components (A), (B) and (C), and to provide excellent feeling upon use and realize an increased cleaning effect. On the other hand, the compositions of Comparative Examples 11 and 12 containing high concentrations of the component (A) and the component (B) were found to insufficiently realize a cleaning effect because the tooth surfaces after use had frictional feeling and were not smooth, and to have bitterness, harshness or salty taste. Further, the compositions of Comparative Examples 13 and 14 not containing the component (A) or the component (B) were found to insufficiently realize a cleaning effect after use as compared to Examples of the present invention.

Example 29 and Comparative Examples 15 and 16

Dentifrice compositions having the compositions shown in Table 7 were prepared and were used for the evaluation of the suppression ratio of adhesion of dirt by three panelists in the same manner as in Example 10 above. Table 7 shows the results of the evaluation.

TABLE 7

| | Composition (mass %) | Example 29 | Comparative Example 15 | Comparative Example 16 |
|---|---|---|---|---|
| (A) | Sodium N-myristoyl-L-glutamate | 0.01 | 0.15 | — |
| (B) | Sodium pyrophosphate | 0.02 | — | — |
| (C) | Sodium lauryl sulfate | 1.4 | 1.4 | 1.4 |
| (D) | Erythritol | 40 | 40 | 40 |
| (G) | Sucralose | 0.01 | 0.01 | 0.01 |
| (E) | Carboxymethyl cellulose | 0.3 | 0.3 | 0.3 |
| | Xanthan gum | 0.05 | 0.05 | 0.05 |
| | Carrageenan | 0.15 | 0.15 | 0.15 |
| (H) | Concentrated glycerin | 4 | 4 | 4 |
| | Sorbitol solution (70%) | 30 | 30 | 30 |
| | Polyethylene glycol | 5 | 5 | 5 |
| | Abrasive silica | 6 | 6 | 6 |
| | Thickening silica | 4.5 | 4.5 | 4.5 |
| | Saccharin sodium | 0.03 | 0.03 | 0.03 |
| | Titanium oxide | 0.3 | 0.3 | 0.3 |
| | Flavor | 1 | 1 | 1 |
| | Purified water | 7.23 | 7.11 | 7.26 |
| | Water content | 16.23 | 16.11 | 16.26 |
| | (B)/(A) | 2 | — | — |
| | (A) + (B) | 0.03 | 0.15 | 0 |
| | (C)/(A) | 140 | 9.3 | — |
| | ((A) + (B))/(G) | 3 | — | — |
| | Suppression ratio of adhesion of protein staining (%) | 30 | 22 | 18 |

The results shown in Table 7 revealed that the oral composition of the present invention (dentifrice composition) containing the N-acylamino acid or the salt thereof, the alkyl sulfate and the pyrophosphoric acid or the salt thereof in specific amounts provided good effect of suppressing the formation of plaque when applied to the oral cavity of a human. That is, the oral composition of the present invention was found to realize an excellent cleaning effect while synergistically enhancing the effect of removing protein staining and the effect of suppressing the adhesion of protein staining, to maintain a good flavor and to significantly contribute to suppression of the formation of plaque.

Examples 30 to 40 and Comparative Examples 17 to 20

Liquid oral compositions having the compositions shown in Tables 8 and 9 were prepared and were used for the evaluation of various properties according to the following methods.

Tables 8 and 9 show the results.

<<Feeling of Tooth Surface after Use>>

The oral cavity was rinsed with 10 mL of each liquid oral composition obtained for 20 seconds, and the composition was discharged. The feeling when tooth surfaces were touched with the tongue immediately after discharge was evaluated according to the following criteria. Two expert panelists evaluated the composition, and Tables 8 and 9 show the results of the evaluation through discussion.

AA: The teeth have smooth surfaces, and the composition realizes an increased cleaning effect.

A: The teeth have slightly coarse surfaces, but the composition realizes a cleaning effect.

B: The teeth have non-smooth surfaces, and the composition poorly realizes a cleaning effect.

C: The teeth have coarse surfaces (feel strong friction on the tooth surfaces).

<<Taste>>

The oral cavity was rinsed with each liquid oral composition obtained for 20 seconds, and the composition was discharged. The taste during rinse and the taste immediately after discharge were evaluated according to the following criteria. Two expert panelists evaluated the composition, and Tables 8 and 9 show the results of the evaluation through discussion.

AA: Feel no foreign taste.
A: Feel almost no foreign taste.
B: Feel slight foreign taste.
C: Feel foreign taste.

<<Low-Temperature Preservation Stability>>

Each liquid oral compositions obtained was placed in a transparent PET container, was preserved at 5° C. for 1 week, and was evaluated for liquid properties according to the following criteria.

AA: Transparent
A: Slightly transparent
B: Contain deposits but turned transparent when returned to room temperature
C: Contain deposits and white turbidness Note that, in the present invention, a transparent oral composition refers to one containing no turbidity and no deposits in appearance regardless of the presence or absence of coloring and having a transmission rate (cell length: 10 mm) of light having a wavelength of 550 nm of 90% or more.

<<Test on Suppression of Calcium Phosphate Adhering Matter>>

9.1 mL of a 13.1 mM $CaCl_2$ solution was taken, and the total volume was adjusted to 70 mL with purified water. Then, 0.18 g of albumin (derived from bovine serum, Wako Pure Chemical Industries, Ltd.) was dissolved in the mixture to prepare a solution. 10 mL of a 40 mM $K_2HPO_4$ solution was added while stirring the solution to achieve final concentrations (Ca concentration: 1.5 mM, P concentration: 5 mM). Hydroxyapatite pellets (PENTAX RICOH IMAGING COMPANY, LTD.) subjected to mirror polishing treatment were immersed in the solution for 30 minutes. The mirror polishing is a method involving performing polishing using three kinds of wrapping films (manufactured by Sumitomo 3M Limited) composed of 40 μm, 12 μm and 3 μm polishing papers with water in the order of fineness, i.e., going from coarser to finer. The pellets were taken out from the solution, immersed in the resultant liquid oral composition for 3 minutes and further immersed in the solution newly prepared and having final concentrations (Ca concentration: 1.5 mM, P concentration: 5 mM). The cycle test was repeated 10 times. After that, the pellets were taken out, and deposits adhering to the surfaces of the pellets were observed by scanning electron microscope. The effect of suppressing the adhesion of the deposits was determined according to the following criteria.

A: No adhering matter.
B: Slight adhering matter on pellet surface.
C: Uniform adhering matter on whole of pellet surface.

<<Evaluation of Acid Resistance>>

10 mL of each liquid oral composition obtained were allowed to act on 0.5 g of hydroxyapatite powder (manufactured by Taihei Chemical Industrial Co., Ltd.) for 10 minutes, and the mixture was centrifuged, followed by removing the supernatant. The residual powder was washed with water, and 5 mL of 0.1 M lactic acid was added and allowed to react for 5 minutes. After that, the supernatant was taken out, and the concentration of calcium ions eluted was measured using Ca Test Wako E (Wako Pure Chemical Industries, Ltd.) and was evaluated based on the following criteria.

A: The concentration of calcium ions was less than 1.5 mM.
B: The concentration of calcium ions was 1.5 mM or more and less than 2 M.
C: The concentration of calcium ions was 2 mM or more.

TABLE 8

| Composition (mass %) | Example 30 | Example 31 | Example 32 | Example 33 | Example 34 | Example 35 | Example 36 | Example 37 | Example 38 | Example 39 | Example 40 |
|---|---|---|---|---|---|---|---|---|---|---|---|
| (A) Sodium N-myristoyl-L-glutamate | 0.05 | 0.05 | 0.05 | — | 0.1 | 0.01 | 0.04 | 0.01 | 0.01 | 0.01 | 0.007 |
| Sodium N-lauroyl-L-glutamate | — | — | — | 0.01 | — | — | — | — | — | — | — |
| (B) Sodium pyrophosphate | 0.1 | 0.1 | 0.1 | 0.02 | 0.4 | 0.4 | 0.02 | 0.4 | 0.4 | 0.4 | 0.1 |
| (F) Polyglyceryl myristate (*1) | 0.25 | — | — | 0.25 | 0.25 | 0.25 | 0.25 | 0.15 | 0.8 | 1 | 0.1 |
| Polyglyceryl laurate (*2) | — | — | — | — | — | — | — | — | — | — | 0.15 |
| Sucrose myristate ester (*3) | — | 0.25 | — | — | — | — | — | — | — | — | — |
| Polyoxyethylene hydrogenated castor oil (40) (*4) | — | — | 0.2 | — | — | — | — | — | — | — | — |

TABLE 8-continued

| Composition (mass %) | Example 30 | Example 31 | Example 32 | Example 33 | Example 34 | Example 35 | Example 36 | Example 37 | Example 38 | Example 39 | Example 40 |
|---|---|---|---|---|---|---|---|---|---|---|---|
| (G) Sucralose | 0.006 | 0.006 | 0.006 | 0.006 | 0.006 | 0.006 | 0.006 | 0.006 | 0.006 | 0.006 | 0.006 |
| (H) Concentrated glycerin | 3 | 3 | 3 | 3 | 3 | 3 | 3 | 3 | 3 | 3 | 3 |
| Sorbitol solution (70%) | 1 | 1 | 1 | 1 | 1 | 1 | 1 | 1 | 1 | 1 | 1 |
| Ethanol | 4 | 4 | 4 | 4 | 4 | 4 | 4 | 4 | 4 | 4 | 4 |
| Citric acid | 0.01 | 0.01 | 0.01 | 0.01 | 0.01 | 0.01 | 0.01 | 0.01 | 0.01 | 0.01 | 0.01 |
| Trisodium citrate | 0.05 | 0.05 | 0.05 | 0.05 | 0.05 | 0.05 | 0.05 | 0.05 | 0.05 | 0.05 | 0.05 |
| Ethyl p-oxybenzoate | 0.05 | 0.05 | 0.05 | 0.05 | 0.05 | 0.05 | 0.05 | 0.05 | 0.05 | 0.05 | 0.05 |
| Flavor | 1 | 1 | 1 | 1 | 1 | 1 | 1 | 0.5 | 1 | 1 | 1 |
| Purified water | 90.484 | 90.484 | 90.534 | 90.604 | 90.134 | 90.224 | 90.574 | 90.824 | 89.674 | 89.474 | 90.527 |
| Water content | 90.784 | 90.784 | 90.834 | 90.904 | 90.434 | 90.524 | 90.874 | 91.124 | 89.974 | 89.774 | 90.827 |
| (B)/(A) | 2 | 2 | 2 | 2 | 4 | 40 | 50 | 40 | 40 | 40 | 14.3 |
| (A) + (B) | 0.15 | 0.15 | 0.15 | 0.03 | 0.5 | 0.41 | 0.06 | 0.41 | 0.41 | 0.41 | 0.107 |
| Evaluation | | | | | | | | | | | |
| Feeling of tooth surface after use | AA | A | AA | A | AA | A | A | A | A | A | A |
| Taste | AA | AA | A | AA | AA | AA | AA | AA | AA | AA | AA |
| Low-temperature preservation stability | AA | AA | AA | AA | AA | AA | A | AA | AA | AA | A |
| Suppression of calcium phosphate deposition | A | A | A | A | A | A | A | A | A | A | A |
| Acid resistance | A | A | A | A | A | A | A | A | A | A | A |

(*1) Sunsoft Q-14Y-C (Taiyo Kagaku Co., Ltd.), average addition molar number: 10, average condensation degree: 9
(*2) Sunsoft Q-12Y-C (Taiyo Kagaku Co., Ltd.), average addition molar number: 10, average condensation degree: 9
(*3) SURFHOPE SE COSME C-1416 (Mitsubishi-Kagaku Foods Corporation)
(*4) EMANON CH-40 (Kao Corporation), average addition molar number of EO: 40

TABLE 9

| Composition (mass %) | | Comparative Example 17 | Comparative Example 18 | Comparative Example 19 | Comparative Example 20 |
|---|---|---|---|---|---|
| (A) | Sodium N-myristoyl-L-glutamate | 0.2 | — | 0.05 | 0.01 |
| (B) | Sodium pyrophosphate | 0.6 | 0.02 | — | 0.5 |
| (F) | Polyglyceryl myristate (*1) | 0.25 | 0.25 | 0.25 | 0.25 |
| (G) | Sucralose | 0.006 | 0.006 | 0.006 | 0.006 |
| (H) | Concentrated glycerin | 3 | 3 | 3 | 3 |
| | Sorbitol solution (70%) | 1 | 1 | 1 | 1 |
| | Ethanol | 4 | 4 | 4 | 4 |
| | Citric acid | 0.01 | 0.01 | 0.01 | 0.01 |
| | Trisodium citrate | 0.05 | 0.05 | 0.05 | 0.05 |
| | Ethyl p-oxybenzoate | 0.05 | 0.05 | 0.05 | 0.05 |
| | Flavor | 1 | 1 | 1 | 1 |
| | Purified water | 89.834 | 90.614 | 90.584 | 6.66 |
| | Water content | 90.134 | 90.914 | 90.884 | 6.96 |
| (B)/(A) | | 3 | — | — | 50 |
| (A) + (B) | | 0.8 | 0.02 | 0.05 | 0.51 |
| Evaluation | | | | | |
| Feeling of tooth surface after use | | B | C | B | C |
| Taste | | C | A | B | C |
| Low-temperature preservation stability | | B | A | C | A |
| Suppression of calcium phosphate deposition | | A | B | C | A |
| Acid resistance | | A | B | C | A |

(*1) Sunsoft Q-14Y-C (Taiyo Kagaku Co., Ltd.), average addition molar number: 10, average condensation degree: 9

The results shown in Tables 8 and 9 reveal that, when the oral compositions of the present invention (liquid oral compositions) including specific amounts of the N-acylamino acid or the salt thereof and the pyrophosphoric acid or the salt thereof at a specific ratio in a specific total amount are applied to the oral cavity of a human, the compositions can provide a good feeling after use, exhibits an excellent effect of suppressing the formation of plaque and have excellent preservation stability under a low-temperature environment and excellent acid resistance.

As mentioned above, the oral composition of the present invention can realize an excellent cleaning effect, while synergistically enhancing the effect of removing protein staining and the effect of suppressing the adhesion of protein staining, can maintain good after taste and can significantly contribute to suppression of plaque formation. Further, the composition was found to be excellent in low-temperature preservation stability and acid resistance.

The invention claimed is:

1. An oral composition, comprising the following components (A) and (B):
   (A) an N-acyl glutamic acid or a salt thereof in an amount of 0.005 mass % or more and 0.3 mass % or less; and
   (B) pyrophosphoric acid or a salt thereof in an amount of 0.005 mass % or more and 0.5 mass % or less,
   wherein a mass ratio ((B)/(A)) of the component (B) to the component (A) is 0.05 or more and 40 or less, and a total content of the component (A) and the component (B) is 0.01 mass % or more and 0.6 mass % or less,
   wherein the acyl group of component (A) is selected from one or more of the group consisting of a lauroyl group, a myristoyl group and a cocoyl group.

2. The oral composition according to claim 1, further comprising component (C) an alkyl sulfate in an amount of 0.5 mass % or more and 2 mass % or less.

3. The oral composition according to claim 2, wherein the mass ratio ((C)/(A)) of component (C) to component (A) is 5 or more and 200 or less.

4. The oral composition according to claim 1, wherein component (B) is pyrophosphoric acid or an alkali metal salt thereof.

5. The oral composition according to claim 1, further comprising component (F) a non-ionic surfactant.

6. The oral composition according to claim 5, wherein component (F) is one or more kinds of fatty acid esters selected from the group consisting of a polyglycerin fatty acid ester and a sucrose fatty acid ester.

7. The oral composition according to claim 1, wherein the total content of component (A) and component (B) is 0.02 mass % or more and 0.45 mass % or less.

8. The oral composition according to claim 1, wherein the mass ratio ((B)/(A)) of component (B) to component (A) is 0.1 or more and 40 or less.

9. The oral composition according to claim 1, further comprising component (D) a sugar alcohol that is dissolved in an aqueous solution at 20° C. in an amount of from 5 to 40 g with respect to 100 g of the aqueous solution.

10. The oral composition according to claim 1, further comprising component (H) glycerin in an amount of 1 mass % or more and 10 mass % or less.

11. The oral composition according to claim 1, wherein the composition is a dentifrice composition.

12. The oral composition according to claim 1, wherein the composition is a liquid oral composition.

13. An oral composition, comprising the following components (A) and (B):
(A) an N-acyl acidic amino acid or a salt thereof in an amount of 0.005 mass % or more and 0.3 mass % or less; and
(B) pyrophosphoric acid or a salt thereof in an amount of 0.005 mass % or more and 0.5 mass % or less,
said composition having a mass ratio ((B)/(A)) of component (B) to component (A) of 0.05 or more and 40 or less, and a total content of component (A) and component (B) of 0.01 mass % or more and 0.6 mass % or less,
wherein component (A) has an acyl group having 6 to 22 carbon atoms.

14. The oral composition according to claim 13, further comprising component (C) an alkyl sulfate in an amount of 0.5 mass % or more and 2 mass % or less.

15. The oral composition according to claim 14, wherein the mass ratio ((C)/(A)) of component (C) to component (A) is 5 or more and 200 or less.

16. The oral composition according to claim 13, wherein component (B) is pyrophosphoric acid or an alkali metal salt thereof.

17. The oral composition according to claim 13, further comprising component (F) a non-ionic surfactant.

18. The oral composition according to claim 17, wherein component (F) is one or more kinds of fatty acid esters selected from the group consisting of a polyglycerin fatty acid ester and a sucrose fatty acid ester.

19. The oral composition according to claim 13, further comprising component (G) sucralose in an amount of 0.001 mass % or more and 0.1 mass % or less.

20. The oral composition according to claim 19, wherein the mass ratio ((A)+(B))/(G) of component (A) and component (B) to component (G) is 1 or more and 30 or less.

21. The oral composition according to claim 1, wherein the amount of component (A) is 0.005-0.1 mass %.

22. The oral composition according to claim 1, wherein component (B) is a sodium or potassium salt of said pyrophosphoric acid.

23. The oral composition according to claim 1, wherein the amount of component (B) is 0.005-0.15 mass %.

24. The oral composition according to claim 1, wherein the total content ((A)+(B)) of component (A) and component (B) is 0.01-0.2 mass %.

25. The oral composition according to claim 3, wherein the mass ratio ((C)/(A)) of component (C) to component (A) is 10-150.

* * * * *